US008241365B2

(12) United States Patent
Williams, Jr. et al.

(10) Patent No.: US 8,241,365 B2
(45) Date of Patent: Aug. 14, 2012

(54) SHOULDER PROSTHESIS WITH VAULT-FILLING STRUCTURE HAVING BONE-SPARING CONFIGURATION

(75) Inventors: Gerald R. Williams, Jr., Villanova, PA (US); Jack F. Long, Warsaw, IN (US); Kyle E. Lappin, Fort Wayne, IN (US); Sarah M. Anthony, Leesburg, IN (US); Stephen R. Donnelly, Willoughby, OH (US); Conrad L. Klotz, Nappanee, IN (US); Joseph P. Iannotti, Strongsville, OH (US)

(73) Assignee: DePuy Products, Inc., Warsaw, IN (US)

( * ) Notice: Subject to any disclaimer, the term of this patent is extended or adjusted under 35 U.S.C. 154(b) by 309 days.

(21) Appl. No.: 12/343,237

(22) Filed: Dec. 23, 2008

(65) Prior Publication Data

US 2010/0161065 A1 Jun. 24, 2010

(51) Int. Cl.
*A61F 2/40* (2006.01)
(52) U.S. Cl. .................................................. 623/19.11
(58) Field of Classification Search ............... 623/18.11, 623/18.12, 19.11, 19.13, 19.14, 20.11–20.13, 623/22.11
See application file for complete search history.

(56) References Cited

U.S. PATENT DOCUMENTS

| | | | |
|---|---|---|---|
| 3,061,977 A | 11/1962 | Schmidt | |
| 3,694,820 A | 10/1972 | Scales et al. | |
| 3,837,008 A | 9/1974 | Bahler et al. | |
| 3,855,638 A | 12/1974 | Pilliar | |
| 4,040,130 A | 8/1977 | Laure | |
| 4,042,980 A | 8/1977 | Swanson et al. | |
| 4,045,825 A | 9/1977 | Stroot | |
| 4,045,826 A | 9/1977 | Stroot | |
| 4,106,128 A | 8/1978 | Greenwald et al. | |
| 4,172,296 A | 10/1979 | D'Errico | |
| 4,180,871 A | 1/1980 | Hamas | |
| 4,524,467 A | 6/1985 | DeCarlo, Jr. | |
| 4,550,450 A | 11/1985 | Kinnett | |
| D285,968 S | 9/1986 | Kinnett | |
| 4,693,723 A | 9/1987 | Gabard | |

(Continued)

FOREIGN PATENT DOCUMENTS

DE     10 2006 041550     11/2007

(Continued)

OTHER PUBLICATIONS

European Search Report in corresponding European application (i.e., EP 09178360), dated May 12, 2010 (7 pages).

(Continued)

*Primary Examiner* — Thomas J Sweet
*Assistant Examiner* — Brian Dukert

(57) ABSTRACT

A shoulder prosthesis includes a vault-filling component defining a bearing-facing surface and having a first coupling component, the vault-filling component including (i) a vault-filling first portion defining a first part of the bearing-facing surface, and (ii) a projecting second portion projecting from the vault-filling first portion so as to define a second part of the bearing-facing surface. The vault-filling first portion and the projecting second portion define a bone space therebetween. The shoulder prosthesis further includes a bearing component defining a bearing surface and having a second coupling component configured to cooperate with the first coupling component to couple the bearing component to the vault-filling component. At least one bone attachment member positioned in the bone space. The projecting second portion of the vault-filling component further defines a scapula-facing surface.

15 Claims, 9 Drawing Sheets

U.S. PATENT DOCUMENTS

| | | | |
|---|---|---|---|
| 4,695,282 | A | 9/1987 | Forte et al. |
| 4,795,468 | A | 1/1989 | Hodorek et al. |
| 4,865,025 | A | 9/1989 | Buzzi et al. |
| 4,865,605 | A | 9/1989 | Dines et al. |
| 4,919,670 | A | 4/1990 | Dale et al. |
| 4,936,853 | A | 6/1990 | Fabian et al. |
| 4,964,865 | A * | 10/1990 | Burkhead et al. .......... 623/19.11 |
| 4,986,833 | A | 1/1991 | Worland |
| 4,987,904 | A | 1/1991 | Wilson |
| 5,030,219 | A | 7/1991 | Matsen, III et al. |
| 5,032,132 | A | 7/1991 | Matsen, III et al. |
| 5,047,058 | A | 9/1991 | Roberts et al. |
| 5,080,673 | A | 1/1992 | Burkhead et al. |
| 5,108,446 | A | 4/1992 | Wagner et al. |
| 5,150,304 | A | 9/1992 | Berchem et al. |
| 5,197,465 | A | 3/1993 | Montgomery |
| 5,201,882 | A | 4/1993 | Paxson |
| 5,304,181 | A | 4/1994 | Caspari et al. |
| 5,314,479 | A | 5/1994 | Rockwood, Jr. et al. |
| 5,344,461 | A | 9/1994 | Phlipot |
| 5,358,526 | A | 10/1994 | Tornier |
| 5,370,693 | A | 12/1994 | Kelman et al. |
| 5,387,241 | A | 2/1995 | Hayes |
| 5,437,677 | A | 8/1995 | Shearer et al. |
| 5,458,637 | A | 10/1995 | Hayes |
| 5,474,559 | A | 12/1995 | Bertin et al. |
| 5,486,180 | A | 1/1996 | Dietz et al. |
| 5,489,309 | A | 2/1996 | Lackey et al. |
| 5,489,310 | A | 2/1996 | Mikhail |
| 5,496,324 | A | 3/1996 | Barnes |
| 5,507,821 | A | 4/1996 | Sennwald et al. |
| 5,554,158 | A | 9/1996 | Vinciguerra et al. |
| 5,593,441 | A | 1/1997 | Lichtenstein et al. |
| 5,593,448 | A | 1/1997 | Dong |
| 5,601,563 | A | 2/1997 | Burke et al. |
| 5,665,090 | A | 9/1997 | Rockwood et al. |
| 5,702,447 | A | 12/1997 | Walch et al. |
| 5,718,360 | A | 2/1998 | Green et al. |
| 5,723,018 | A | 3/1998 | Cyprien et al. |
| 5,743,915 | A | 4/1998 | Bertin et al. |
| 5,769,855 | A | 6/1998 | Bertin et al. |
| 5,779,710 | A | 7/1998 | Matsen, III |
| 5,782,924 | A | 7/1998 | Johnson |
| 5,800,551 | A | 9/1998 | Williamson et al. |
| 5,853,415 | A | 12/1998 | Bertin et al. |
| 5,860,981 | A | 1/1999 | Bertin et al. |
| 5,879,401 | A | 3/1999 | Besemer et al. |
| 5,908,424 | A | 6/1999 | Bertin et al. |
| 5,928,285 | A | 7/1999 | Bigliani et al. |
| 5,976,145 | A | 11/1999 | Kennefick, III |
| 6,045,582 | A | 4/2000 | Prybyla |
| 6,096,084 | A | 8/2000 | Townley |
| 6,139,581 | A | 10/2000 | Engh et al. |
| 6,197,062 | B1 | 3/2001 | Fenlin |
| 6,197,063 | B1 | 3/2001 | Dews |
| 6,206,925 | B1 | 3/2001 | Tornier |
| 6,228,119 | B1 | 5/2001 | Ondrla et al. |
| 6,228,900 | B1 | 5/2001 | Shen et al. |
| 6,245,074 | B1 | 6/2001 | Allard et al. |
| 6,281,264 | B1 | 8/2001 | Salovey et al. |
| 6,364,910 | B1 | 4/2002 | Shultz et al. |
| 6,368,353 | B1 | 4/2002 | Arcand |
| 6,379,386 | B1 | 4/2002 | Resch et al. |
| 6,406,495 | B1 | 6/2002 | Schoch |
| 6,488,715 | B1 | 12/2002 | Pope et al. |
| 6,514,287 | B2 | 2/2003 | Ondrla |
| 6,620,197 | B2 | 9/2003 | Maroney et al. |
| 6,673,115 | B2 | 1/2004 | Resch et al. |
| 6,676,705 | B1 | 1/2004 | Wolf |
| 6,679,916 | B1 | 1/2004 | Frankle et al. |
| 6,699,289 | B2 | 3/2004 | Iannotti et al. |
| 6,783,549 | B1 | 8/2004 | Stone et al. |
| 6,875,234 | B2 | 4/2005 | Lipman et al. |
| 6,893,702 | B2 | 5/2005 | Takahashi |
| 6,896,702 | B2 | 5/2005 | Collazo |
| 6,899,736 | B1 | 5/2005 | Rauscher et al. |
| 6,911,047 | B2 | 6/2005 | Rockwood, Jr. et al. |
| 6,942,699 | B2 | 9/2005 | Stone et al. |
| 6,953,478 | B2 | 10/2005 | Bouttens et al. |
| 7,033,396 | B2 | 4/2006 | Tornier |
| 7,051,451 | B2 | 5/2006 | Augostino et al. |
| 7,090,677 | B2 | 8/2006 | Fallin et al. |
| 7,160,328 | B2 | 1/2007 | Rockwood, Jr. et al. |
| 7,160,331 | B2 | 1/2007 | Cooney, III et al. |
| 7,169,184 | B2 | 1/2007 | Dalla Pria |
| 7,175,665 | B2 | 2/2007 | German et al. |
| 7,204,854 | B2 | 4/2007 | Guederian et al. |
| 7,329,284 | B2 | 2/2008 | Maroney et al. |
| 7,527,631 | B2 | 5/2009 | Maroney et al. |
| 7,604,665 | B2 | 10/2009 | Iannotti et al. |
| 7,608,109 | B2 | 10/2009 | Dalla Pria |
| 7,621,961 | B2 | 11/2009 | Stone |
| 7,625,408 | B2 | 12/2009 | Gupta et al. |
| 7,753,959 | B2 | 7/2010 | Berelsman et al. |
| 7,766,969 | B2 | 8/2010 | Justin et al. |
| 7,892,287 | B2 | 2/2011 | Deffenbaugh |
| 7,922,769 | B2 | 4/2011 | Deffenbaugh et al. |
| 7,927,335 | B2 | 4/2011 | Deffenbaugh et al. |
| 2001/0010636 | A1 | 8/2001 | Gotou |
| 2001/0011192 | A1 | 8/2001 | Ondrla et al. |
| 2001/0018589 | A1 | 8/2001 | Muller |
| 2001/0030339 | A1 | 10/2001 | Sandhu et al. |
| 2001/0037153 | A1 | 11/2001 | Rockwood, Jr. et al. |
| 2002/0004685 | A1 | 1/2002 | White |
| 2002/0082702 | A1 | 6/2002 | Resch et al. |
| 2002/0099445 | A1 | 7/2002 | Maroney et al. |
| 2003/0028253 | A1 | 2/2003 | Stone et al. |
| 2003/0045883 | A1 | 3/2003 | Chow et al. |
| 2003/0055507 | A1 | 3/2003 | McDevitt et al. |
| 2003/0065397 | A1 | 4/2003 | Hanssen et al. |
| 2003/0097183 | A1 | 5/2003 | Rauscher et al. |
| 2003/0114933 | A1 | 6/2003 | Bouttens et al. |
| 2003/0125809 | A1* | 7/2003 | Iannotti et al. ............. 623/19.13 |
| 2003/0149485 | A1 | 8/2003 | Tornier |
| 2003/0187514 | A1 | 10/2003 | McMinn |
| 2004/0064189 | A1 | 4/2004 | Maroney et al. |
| 2004/0122519 | A1 | 6/2004 | Wiley et al. |
| 2004/0122520 | A1 | 6/2004 | Lipman et al. |
| 2004/0162619 | A1 | 8/2004 | Blaylock et al. |
| 2004/0193277 | A1 | 9/2004 | Long et al. |
| 2004/0193278 | A1 | 9/2004 | Maroney et al. |
| 2004/0220673 | A1 | 11/2004 | Pria |
| 2004/0220674 | A1 | 11/2004 | Pria |
| 2004/0230312 | A1 | 11/2004 | Hanson et al. |
| 2004/0236424 | A1 | 11/2004 | Berez et al. |
| 2005/0021148 | A1 | 1/2005 | Gibbs |
| 2005/0049709 | A1 | 3/2005 | Tornier |
| 2005/0125068 | A1 | 6/2005 | Hozack et al. |
| 2005/0171613 | A1 | 8/2005 | Sartorius et al. |
| 2005/0261775 | A1 | 11/2005 | Baum et al. |
| 2006/0030946 | A1 | 2/2006 | Ball et al. |
| 2006/0069443 | A1 | 3/2006 | Deffenbaugh et al. |
| 2006/0069444 | A1 | 3/2006 | Deffenbaugh |
| 2006/0074353 | A1 | 4/2006 | Deffenbaugh et al. |
| 2006/0074430 | A1 | 4/2006 | Deffenbaugh et al. |
| 2006/0079963 | A1 | 4/2006 | Hansen |
| 2006/0100498 | A1 | 5/2006 | Boyce et al. |
| 2006/0100714 | A1 | 5/2006 | Ensign |
| 2006/0111787 | A1 | 5/2006 | Bailie et al. |
| 2006/0149387 | A1 | 7/2006 | Smith et al. |
| 2006/0149388 | A1 | 7/2006 | Smith et al. |
| 2006/0161260 | A1 | 7/2006 | Thomas et al. |
| 2007/0055380 | A1 | 3/2007 | Berelsman et al. |
| 2007/0142917 | A1 | 6/2007 | Roche et al. |
| 2007/0179624 | A1 | 8/2007 | Stone et al. |
| 2007/0219637 | A1 | 9/2007 | Berelsman et al. |
| 2007/0219638 | A1 | 9/2007 | Jones et al. |
| 2007/0225817 | A1 | 9/2007 | Reubelt et al. |
| 2008/0046091 | A1 | 2/2008 | Weiss et al. |
| 2008/0140209 | A1 | 6/2008 | Iannotti et al. |
| 2008/0208348 | A1 | 8/2008 | Fitz |
| 2008/0234820 | A1 | 9/2008 | Felt et al. |
| 2009/0125113 | A1 | 5/2009 | Guederian et al. |
| 2009/0143865 | A1 | 6/2009 | Hassler et al. |
| 2009/0204225 | A1 | 8/2009 | Meridew et al. |
| 2009/0281630 | A1 | 11/2009 | Delince et al. |

| | | | |
|---|---|---|---|
| 2009/0292364 A1 | 11/2009 | Linares | |
| 2009/0312839 A1 | 12/2009 | Scheker et al. | |
| 2010/0049327 A1 | 2/2010 | Isch et al. | |

FOREIGN PATENT DOCUMENTS

| | | |
|---|---|---|
| DE | 102008021110 A1 | 10/2009 |
| EP | 0103246 A1 | 3/1984 |
| EP | 0339530 A2 | 2/1989 |
| EP | 0329854 A1 | 8/1989 |
| EP | 0538895 A2 | 4/1993 |
| EP | 0538895 A3 | 4/1993 |
| EP | 0581667 | 2/1994 |
| EP | 0776636 | 6/1997 |
| EP | 0903127 A2 | 3/1999 |
| EP | 1013246 | 6/2000 |
| EP | 1064890 | 1/2001 |
| EP | 1402853 | 3/2004 |
| EP | 1639966 | 3/2006 |
| EP | 1639967 | 3/2006 |
| EP | 1902689 | 3/2008 |
| FR | 1064890 | 5/1954 |
| FR | 2578162 | 9/1986 |
| FR | 2579454 | 10/1986 |
| FR | 2652498 A1 | 5/1991 |
| FR | 2683142 A1 | 5/1993 |
| FR | 2695313 A1 | 3/1994 |
| FR | 2704747 | 11/1994 |
| FR | 2755847 A1 | 5/1998 |
| FR | 2776506 | 10/1999 |
| FR | 2825263 A1 | 12/2002 |
| GB | 2297257 A | 7/1996 |
| WO | 0134040 A1 | 5/2001 |
| WO | 02067821 A2 | 9/2002 |
| WO | 02067821 A3 | 9/2002 |
| WO | 03005933 A2 | 1/2003 |
| WO | 03005933 A3 | 1/2003 |
| WO | 03030770 A2 | 4/2003 |
| WO | 2007096741 A2 | 8/2007 |
| WO | 2011098890 A1 | 8/2011 |

OTHER PUBLICATIONS

Biomet Corporation, Biomet Biomodular Low Profile Modular Glenoid, Surgical Technique, available at least as early as Dec. 22, 2008, one (1) page.

Biomet Corporation, Biangular Standard Metal Backed Glenoid, 1996, one (1) page.

Kirschner Medical Corporation, Kirschner Integrated Shoulder System for Hemi & Total Shoulder Arthroplasty, Surgical Technique, available at least as early as Dec. 22, 2008, two (2) pages.

Smith & Nephew Richards, Inc., The Cofield Total Shoulder System, available at least as early as Dec. 22, 2008, two (2) pages.

European Search Report in European application EP99304423, mailed Sep. 17, 1999, three (3) pages.

English Language Translation of FR2652498A1, Inventor Michael Columbier, Date of Publ. Oct. 4, 1989.

English Language Translation of EP0339530, Inventor Hans Grundle, Date of Publ. Nov. 2, 1989.

English Language Translation of Abstract to FR2704747, Inventor Didier Capon et al., Date of Publ. Nov. 10, 1994.

English Language Translation of Abstract to FR2776506, Inventor Katz Denis et al., Date of Publ. Oct. 1, 1999.

* cited by examiner

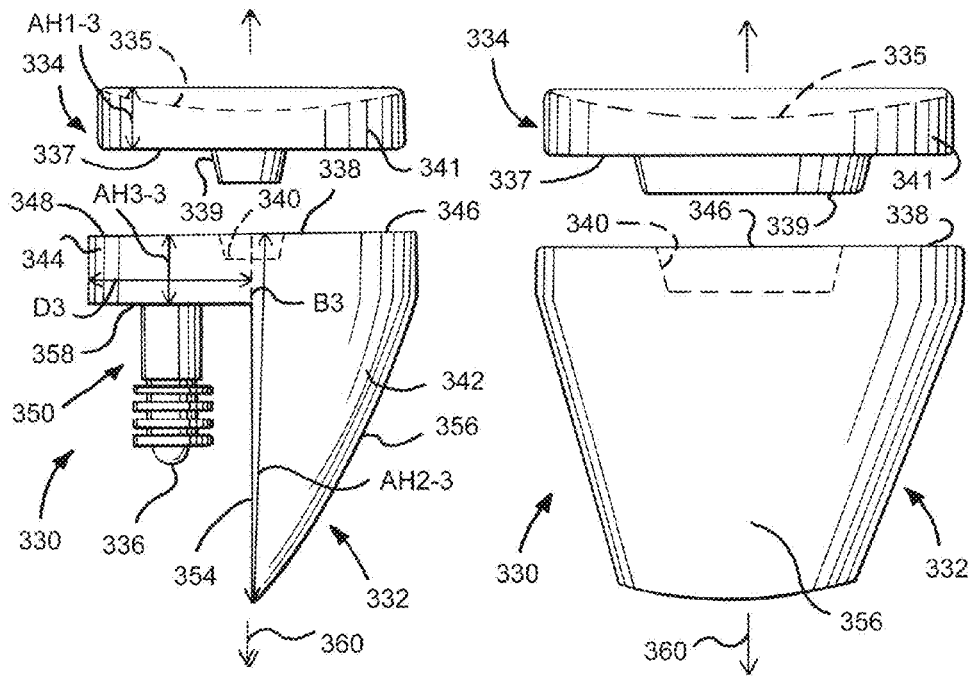
FIG. 13
FIG. 14
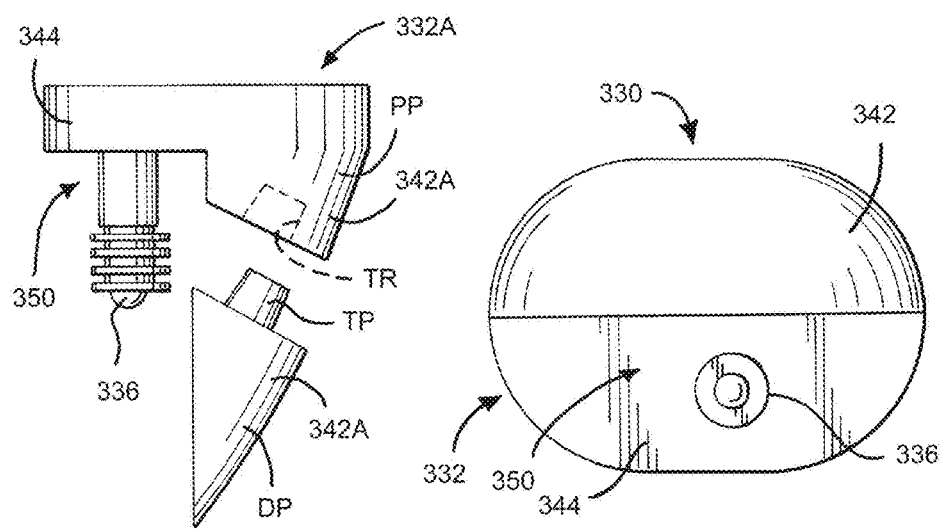
FIG. 13A
FIG. 15

SHOULDER PROSTHESIS WITH VAULT-FILLING STRUCTURE HAVING BONE-SPARING CONFIGURATION

BACKGROUND

The present disclosure relates generally to shoulder prostheses, and more particularly to shoulder prostheses configured for use in shoulders having glenoid vault erosion or defects.

A typical shoulder or glenohumeral joint is formed in a human body where the humerus 10 movably contacts the scapula 12 as shown in FIG. 1. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. During the lifetime of a patient, the glenoid fossa 14 may become worn, especially at its posterior portion thereby causing severe shoulder pain and limiting the range of motion of the patient's shoulder joint. To alleviate such pain and increase the patient's range of motion, a shoulder arthroplasty may be performed.

Shoulder arthroplasty often involves surgical replacement of the glenoid fossa with a conventional glenoid prosthesis such as the one disclosed in U.S. Pat. No. 6,911,047, the disclosure of which is herein incorporated by reference. The glenoid prosthesis, when implanted, provides a new laterally-facing concave bearing surface for articulation with a complementary bearing surface of a natural or prosthetic humeral head. Such conventional glenoid prosthesis is typically formed from UHMW polyethylene, and includes bone anchor(s) such as peg(s) or a keel extending from a back side of the device opposite its bearing surface. So configured, the back side of the prosthesis is typically secured against subchondral bone of the glenoid vault while the bone anchor(s) may extend into the cavity of the glenoid vault whereby it may become anchored to cancellous bone located within the glenoid vault.

However, the subchondral bone support surface and underlying cancellous bone located within the glenoid vault may be significantly deteriorated such that support and anchoring of the conventional glenoid prosthesis may be difficult. Inadequate support and anchoring of the glenoid prosthesis may lead to loosening of the glenoid prosthesis whereby accelerated wear and then failure of the prosthesis may occur.

One document that attempts to address this issue is U.S. Pat. No. 7,329,284 (hereinafter "the '284 patent"), the disclosure of which is herein incorporated by reference. In this document, a prosthetic glenoid component is disclosed that includes a stem portion configured to substantially fill the glenoid vault. While this type of device provides significant advantages for patients having substantially complete erosion of the subchondral and cancellous bone within the glenoid vault, some patients have a significant amount of subchondral and cancellous bone remaining even though partial erosion of the subchondral and cancellous bone has occurred. Removal of healthy subchondral and/or cancellous bone stock in these latter types of patients in order to utilize a prosthesis of the type disclosed in the '284 patent may have disadvantages.

What is needed therefore is an improved shoulder prosthesis for use in patients having deterioration of their subchondral support surface and underlying cancellous bone of their glenoid vault. What is further needed is an improved shoulder prosthesis for use in a patients having deterioration of their subchondral support surface and underlying cancellous bone who still have some healthy bone stock remaining in their glenoid vault.

SUMMARY

In accordance with one embodiment of the present disclosure, there is provided a shoulder prosthesis that includes a vault-filling component defining a bearing-facing surface and having a first coupling component. The vault-filling component includes (i) a vault-filling first portion defining a first part of the bearing-facing surface, and (ii) a projecting second portion projecting from the vault-filling first portion so as to define a second part of the bearing-facing surface. The vault-filling first portion and the projecting second portion define a bone space therebetween. The shoulder prosthesis further includes a bearing component defining a bearing surface and having a second coupling component configured to cooperate with the first coupling component to couple the bearing component to the vault-filling component. At least one bone attachment member is positioned in the bone space. The projecting second portion of the vault-filling component further defines a scapula-facing surface. The vault-filling first portion of the vault-filling component further defines (i) a first lateral surface extending from the scapula-facing surface, and (ii) a second lateral surface extending from the first part of the bearing-facing surface. The first lateral surface and the second lateral surface taper towards each other in a direction extending away from the bearing-facing surface.

Pursuant to another embodiment of the present disclosure, there is provided a shoulder prosthesis that includes a metallic vault-filling component defining a bearing-facing surface and having a first coupling component. The metallic vault-filling component includes (i) a metallic vault-filling first portion defining a first part of the bearing-facing surface, and (ii) a metallic projecting second portion projecting from the metallic vault-filling first portion so as to define a second part of the bearing-facing surface, the metallic vault-filling first portion and the metallic projecting second portion defining a bone space therebetween. The shoulder prosthesis further includes a polymeric bearing component defining a bearing surface and having a second coupling component configured to cooperate with the first coupling component to couple the polymeric bearing component to the metallic vault-filling component. The metallic projecting second portion of the metallic vault-filling component further defines a scapula-facing surface. The metallic vault-filling first portion of the metallic vault-filling component further defines (i) a first lateral surface extending from the scapula-facing surface, and (ii) a second lateral surface extending from the first part of the bearing-facing surface. The first lateral surface and the second lateral surface taper towards each other in a direction extending away from the bearing-facing surface.

In accordance with yet another embodiment of the present disclosure, there is provided a shoulder prosthesis that includes a vault-filling component defining a bearing-facing surface and having a first coupling component. The vault-filling component includes (i) a vault-filling first portion defining a first part of the bearing-facing surface, and (ii) a projecting second portion projecting from the vault-filling first portion so as to define a second part of the bearing-facing surface, the vault-filling first portion and the projecting second portion defining a bone space therebetween. The shoulder prosthesis further includes a bearing component defining a bearing surface and having a second coupling component configured to cooperate with the first coupling component to couple the bearing component to the vault-filling component.

The bearing component possesses a first maximum axial height of at least 3.0 mm. The vault-filling first portion possesses a second maximum axial height of at least 15.0 mm. The projecting second portion possesses a third maximum axial height of at least 1.0 mm. The projecting second portion extends from the vault-filling first portion for a maximum distance of at least 2.0 mm.

BRIEF DESCRIPTION OF THE DRAWINGS

FIG. 13 is a side elevational view of yet another alternative embodiment of the shoulder prosthesis of the present disclosure;

FIG. 13A is a view similar to FIG. 13, but showing an alternative embodiment of a vault-filling component that is usable with the shoulder prosthesis of FIG. 13;

FIG. 14 is another side elevational view of the shoulder prosthesis of FIG. 13;

FIG. 15 is a bottom elevational view of the shoulder prosthesis of FIG. 13;

DESCRIPTION OF THE PREFERRED EMBODIMENTS

Figure 1:
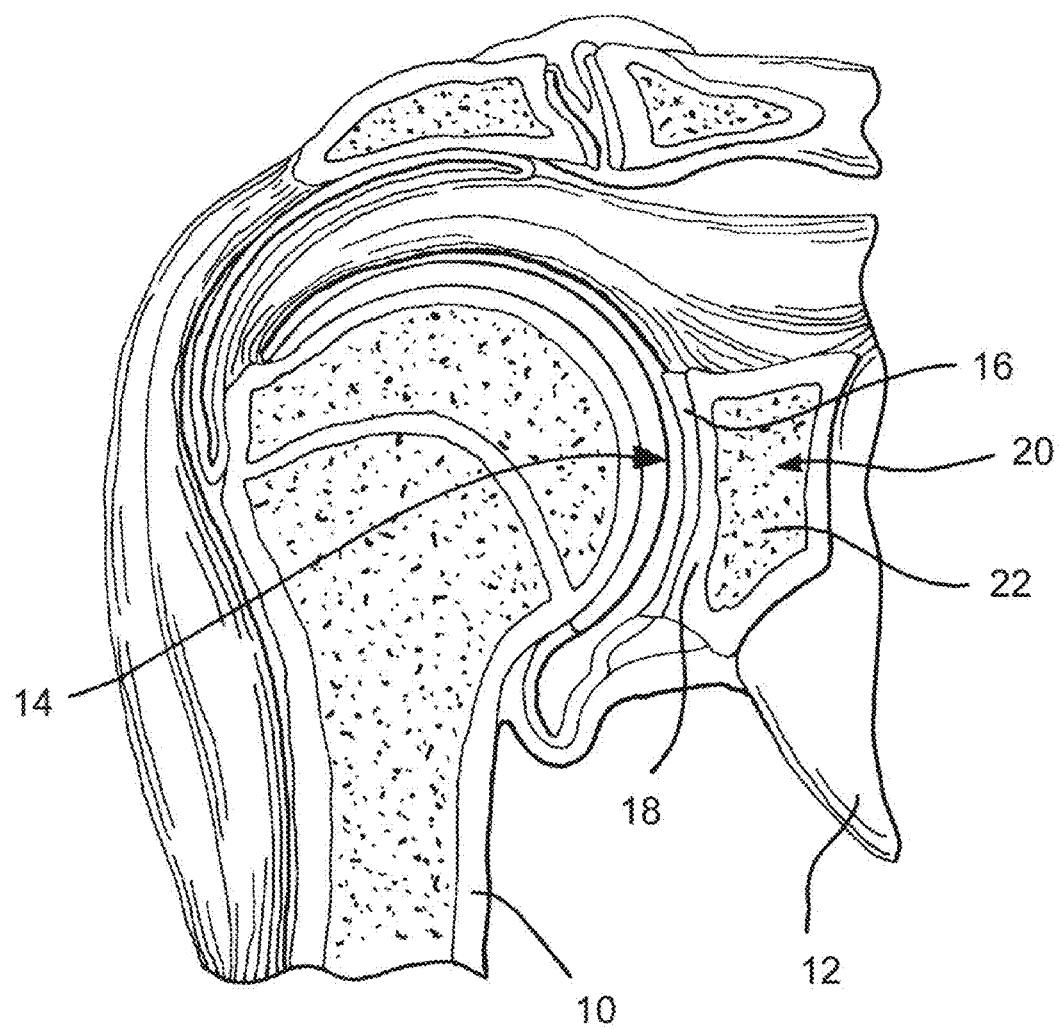
FIG. 1 is a cross-sectional view of an anatomically normal glenohumeral joint of a human patient.

While the shoulder prosthesis described herein is susceptible to various modifications and alternative forms, specific embodiments thereof have been shown by way of example in the drawings and will herein be described in detail. It should be understood, however, that there is no intent to limit the shoulder prosthesis to the particular forms disclosed, but on the contrary, the intention is to cover all modifications, equivalents, and alternatives falling within the spirit and scope of the invention as defined by the appended claims.

Referring now to FIGS. 2-7, there is shown a shoulder prosthesis 30 that includes a vault-filling component 32 and a bearing component 34. The shoulder prosthesis 30 further includes a number of bone attachment members 36A, 36B, 36C. In the embodiment shown in FIGS. 2-7, the bone attachment members 36A, 36B, 36C are externally threaded bone screws. Each bone screw 36A, 36B, 36C includes a hex shaped recess configured to receive an end of a driver tool (not shown) configured to rotate the bone screws with respect to the vault-filling component 32.

The vault-filling component 32 is made entirely of a metallic material, while the bearing component 34 is made entirely of a polymeric material. Preferably, the vault-filling component 32 is made a biological grade stainless steel or titanium material. Also, the vault-filling component 32 may include a porous-coating on its entire outer surface (except for its bearing-facing surface described below) to facilitate biological ingrowth of a patient's bone. The bearing component 34 is preferably made entirely of a polymer such as polyethylene. One particular polyethylene that is well suited for use as the bearing component is a high molecular weight polyethylene, for example, ultra-high molecular weight polyethylene (UHMWPE).

Figure 4:
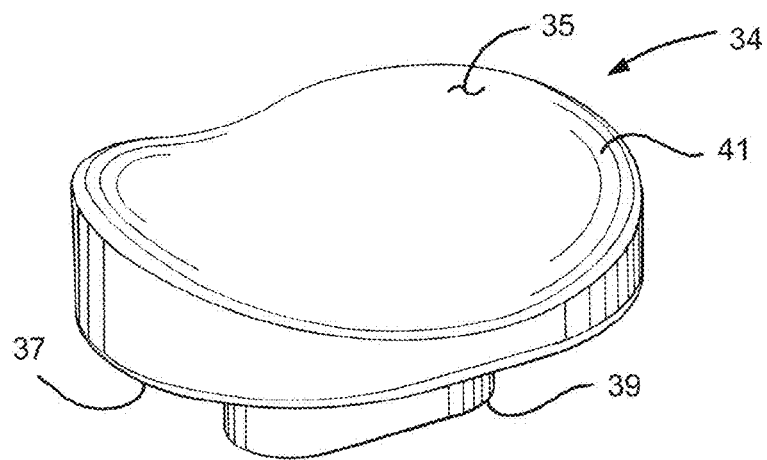
FIG. 4 is a perspective view of the bearing component of the shoulder prosthesis of FIG. 2.
Figure 5:
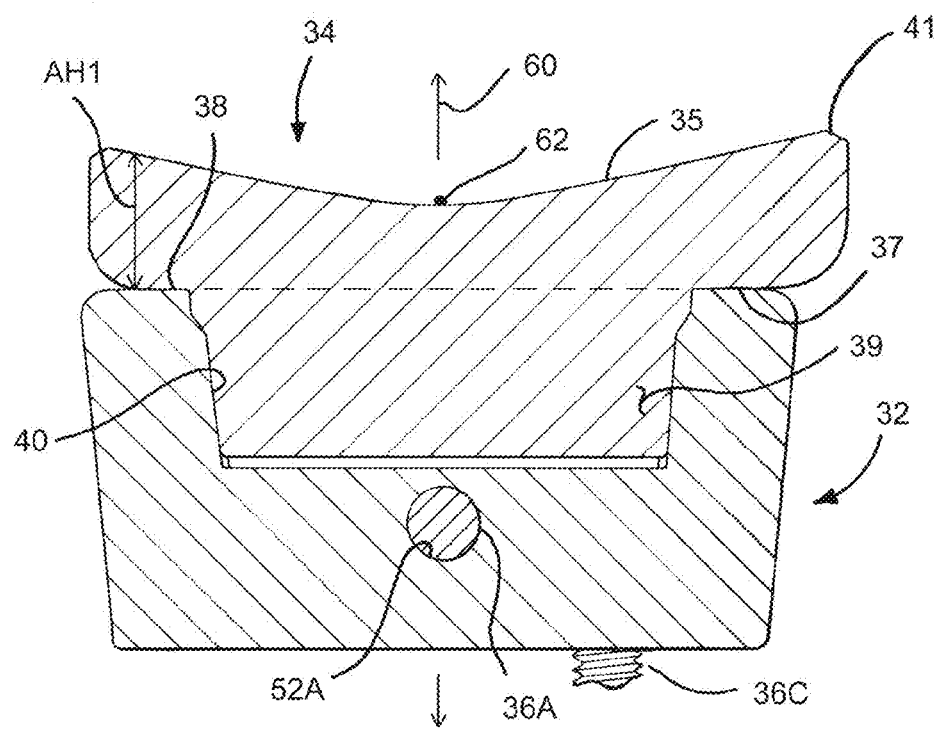
FIG. 5 is a cross-sectional view taken along the line 5-5 of FIG. 2 in the direction of the arrows, with only a fragment of bone screw 36C shown for clarity of viewing.

FIGS. 4-5 show the bearing component 34 in more detail. The bearing component 34 includes a bearing body 41 that defines a bearing surface 35. The bearing surface 35 is a concave bearing surface configured to mate with a head of a natural humerus such as humerus 10 shown in FIG. 1 or a similarly configured prosthetic humerus. However, if the shoulder prosthesis 30 is used with a humeral prosthesis that includes a head having a concave bearing surface, then the bearing surface 35 would alternatively be configured as a convex bearing surface. The bearing body 41 of the bearing component 34 further defines a scapula-facing surface 37 which is located on its back side opposite in relation to the bearing surface 35 as shown in FIGS. 4-5. The bearing component 34 further includes a coupling component 39 extending from the scapula-facing surface 37. In the embodiment of FIGS. 2-7, the coupling component 39 is a tapered post.

Figure 6:
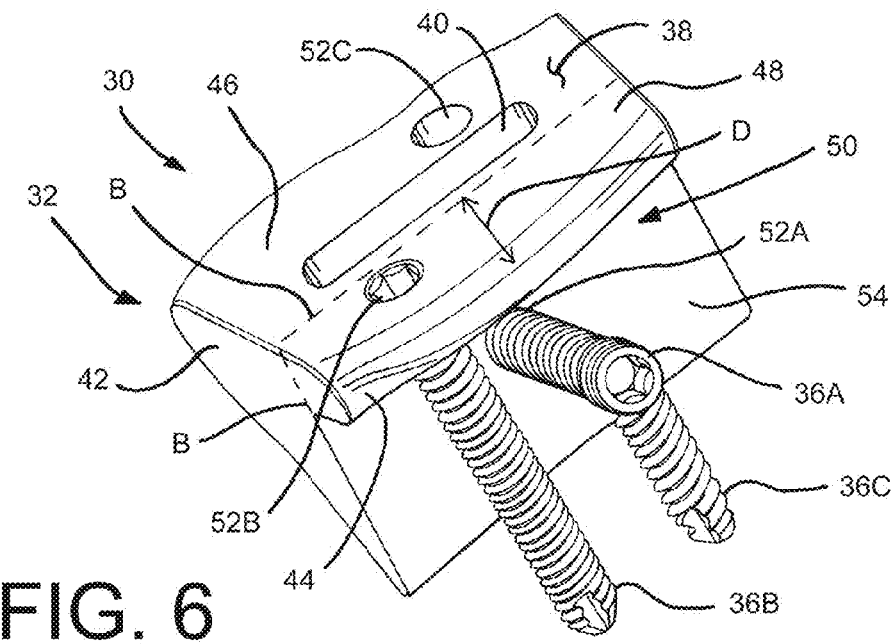
FIG. 6 is a view similar to FIG. 2, except with the bearing component shown removed for clarity of viewing.
Figure 7:
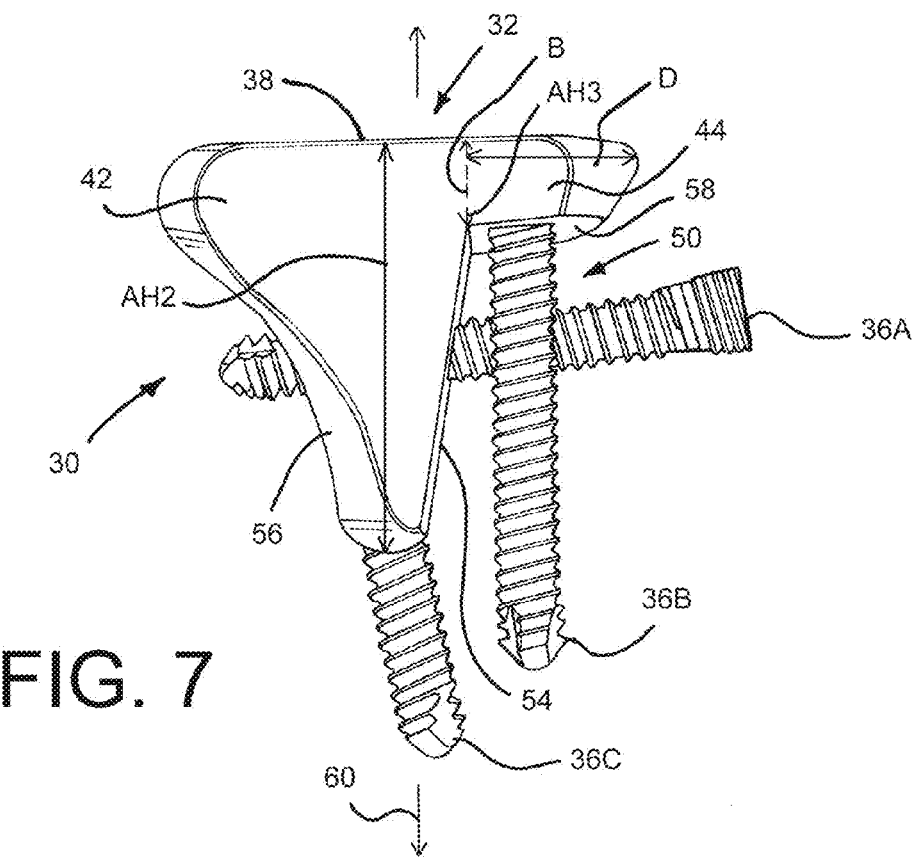
FIG. 7 is a side elevational view of the vault-filling component and the bone screws of FIG. 6.

FIGS. 6-7 show the shoulder prosthesis 30 with the bearing component 34 removed for clarity of description. The vault-filling component 32 defines a bearing-facing surface 38. The vault-filling component 32 includes a coupling component 40 defined by a tapered recess as shown in FIG. 5. The tapered recess 40 and the tapered post 39 are configured to cooperate with each other to couple the bearing component 34 to the vault-filling component 32 as shown in FIG. 5. In particular, the tapered post 39 is received within the tapered recess 40 in a friction fit manner.

Figure 2:
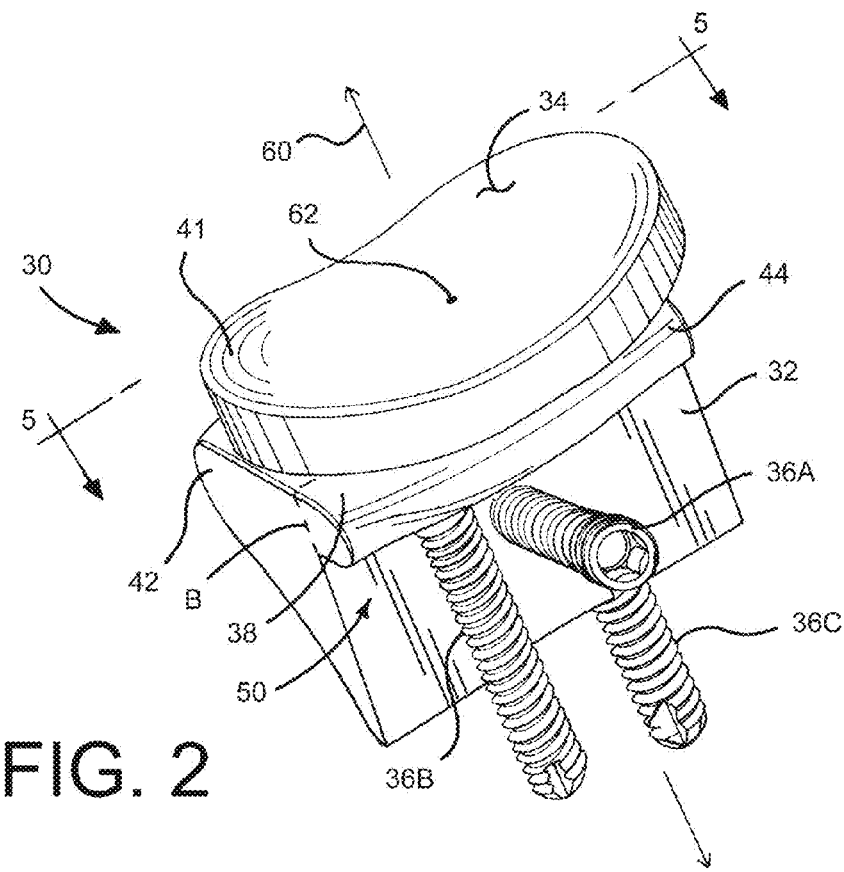
FIG. 2 is a perspective view of a shoulder prosthesis of the present disclosure.
Figure 3:
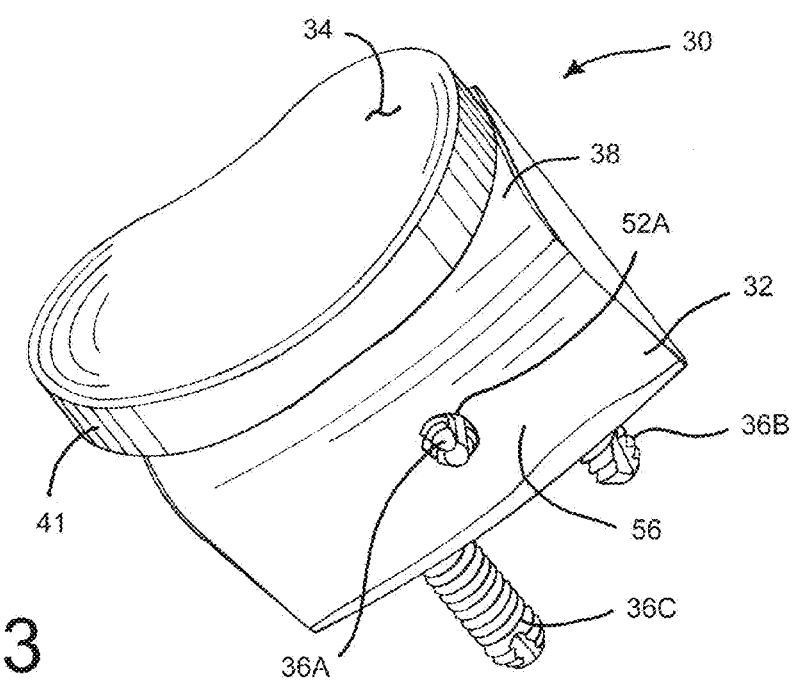
FIG. 3 is another perspective view of the shoulder prosthesis of FIG. 2.

The vault-filling component 32 includes a vault-filling first portion 42 and a projecting second portion 44 which projects from the vault-filling first portion for a maximum distance D as shown in FIGS. 6-7. The maximum distance D is preferably at least 2.0 mm. However, the maximum distance D may be much greater than 2.0 mm. For example, the maximum distance D may be 5.0 mm or 7.0 mm. The vault-filling first portion 42 and the projecting second portion 44 are integrally formed together to form the vault-filling component. The vault-filling first portion 42 defines a first part 46 of the bearing-facing surface 38, while the projecting second portion 44 defines a second part 48 of the bearing-facing surface 38. A bone space 50 is defined between the vault-filling first portion 42 and the projecting second portion 44. As shown in FIGS. 2, 4, and 5, bone attachment members 36A, 36B are positioned within the bone space 50.

The vault-filling component 32 further defines an internally threaded fastener passage 52A, an internally threaded fastener passage 52B, and an internally threaded fastener passage 52C each extending through the component 32. The externally threaded bone screw 36A is meshingly received in the internally threaded fastener passage 52A. Similarly, the externally threaded bone screw 36B is meshingly received in the internally threaded fastener passage 52B, while the externally threaded bone screw 36C is meshingly received in the internally threaded fastener passage 52C. Rotation of each screw 36A, 36B, 36C with the fastener tool (not shown) causes advancement of each screw 36A, 36B, 36C in relation to the vault-filling component 32.

The vault-filling first portion 42 further defines a lateral surface 54 and an opposite lateral surface 56. The term "lateral" as used herein with surfaces 54, 56 means "of or relating to the sides of the vault-filling first portion 42" as opposed to any type of relation to a patient's body (e.g. medial or lateral side of a patient). The internally threaded fastener passage 52A extends from the lateral surface 54 to the lateral surface 56. The projecting second portion 44 further defines a scapula-facing surface 58. The lateral surface 54 extends downwardly from the scapula-facing surface 58 as shown in FIGS. 6-7, while the lateral surface 56 extends downwardly from the first part 46 of the bearing-facing surface 38. These two surfaces 54, 56 converge in a downward direction to meet near a distal end of the first portion 42 as shown in FIGS. 6-7. The internally threaded fastener passage 52B extends from the second part 48 of the bearing-facing surface to the scapula-facing surface 58. So configured, the vault-filling component 32 is configured to direct bone screws 36A, 36B through the bone space 50 so as to anchor to cancellous bone (e.g. cancellous bone 22 of FIG. 1). In addition, the internally threaded fastener passage 52C extends from the first part 46 of the bearing-facing surface to a back surface of the vault-filling first portion 42.

The shoulder prosthesis 30 defines an axis 60 which is generally aligned with a center 62 of the bearing surface 34. In the embodiment of FIGS. 2-7, the bearing surface 34 is symmetrical about the axis 60. When implanted, the axis 60 will generally be aligned with the center of the patient's natural glenoid fossa (e.g. the glenoid fossa 16 shown in FIG. 1).

The bearing body 41 of the bearing component 34 possesses a maximum axial height AH1 (see FIG. 5) that represents the maximum height of the bearing body measured in a direction parallel to the axis 60. In addition, the vault-filling first portion 42 possesses a maximum axial height AH2 (see FIG. 7), while the projecting second portion 44 possesses a maximum axial height AH3 (see FIG. 7), where both AH2 and AH3 represent maximum heights of the components (i.e. first and projecting second portions 42, 44) measured in the direction parallel to the axis 60. Note that in the embodiment of FIGS. 2-7, the maximum axial height of the projecting second portion 44 occurs at a location juxtaposed to a boundary line B between the vault-filling first portion 42 and the projecting second portion 44 as shown in FIG. 7.

Preferably, the maximum axial height AH1 is at least 3.0 mm, and the maximum axial height AH2 is at least 15.0 mm, while the maximum axial height AH3 is at least 1.0 mm. However, it should be appreciated that the maximum axial heights AH1, AH2, and AH3 may be well above these minimum magnitudes. For example, AH1 may be equal to 4.0 mm, while AH2 may be equal to 20.0 mm, and AH3 may be equal to 5.0 mm. It is believed that configuring the shoulder prosthesis 30 with maximum axial heights AH1, AH2, and AH3 that possess the magnitudes discussed above results in an improved shoulder prosthesis that is usable in a patients having deterioration of their subchondral support surface and underlying cancellous bone that still have some healthy bone stock remaining in their glenoid vault.

Turning now to FIGS. 8-11, there is shown another embodiment of a shoulder prosthesis 130 that is used in substantially the same manner as the shoulder prosthesis 30 described hereinabove. The shoulder prosthesis 130 includes a vault-filling component 132 and a bearing component 134. Note that the bearing component 134 possesses the exact same dimensions and configuration as the bearing component 34, with one exception. In particular, the bearing component 134 includes a coupling component in the form of a tapered post 139 that possesses a different configuration in comparison to the tapered post 39 of the shoulder prosthesis 30 of FIGS. 2-7. (See FIG. 8.) The shoulder prosthesis 130 further includes a number of bone attachment members 136A, 136B. The bone attachment members 136A, 136B are externally threaded bone screws. Each bone screw 136A, 136B includes a hex shaped recess configured to receive an end of a driver tool (not shown) configured to rotate the bone screws with respect to the vault-filling component 132.

The vault-filling component 132 is made entirely of a metallic material, while the bearing component 134 is made entirely of a polymeric material. Preferably, the vault-filling component 132 is made of the same material from which the vault-filling component 32 is made which was described above. In addition, the bearing component 134 is made of the same material from which the bearing component 34 is made which was also described above.

The vault-filling component 132 defines a bearing-facing surface 138. One difference between the vault-filling component 32 of the previous embodiment and the vault-filling component 132 of the current embodiment is that the vault-filling component 132 includes an insert 143 that is configured to be received in a friction fit manner in a recess 145 defined in the bearing-facing surface 138. The insert 143 is made of a metallic material such as a biological grade stainless steel or titanium material. The insert 143 includes an outer surface that engages the inner surface defined by the recess 145 so as to couple the insert 143 to the vault-filling component 132. The insert 143 further defines a recess 147 that is configured and dimensioned to receive the tapered post 139 of the bearing component 134 in a friction fit manner so as to couple the bearing component 134 to a base 134B of the vault-filling component 132.

Figure 8:
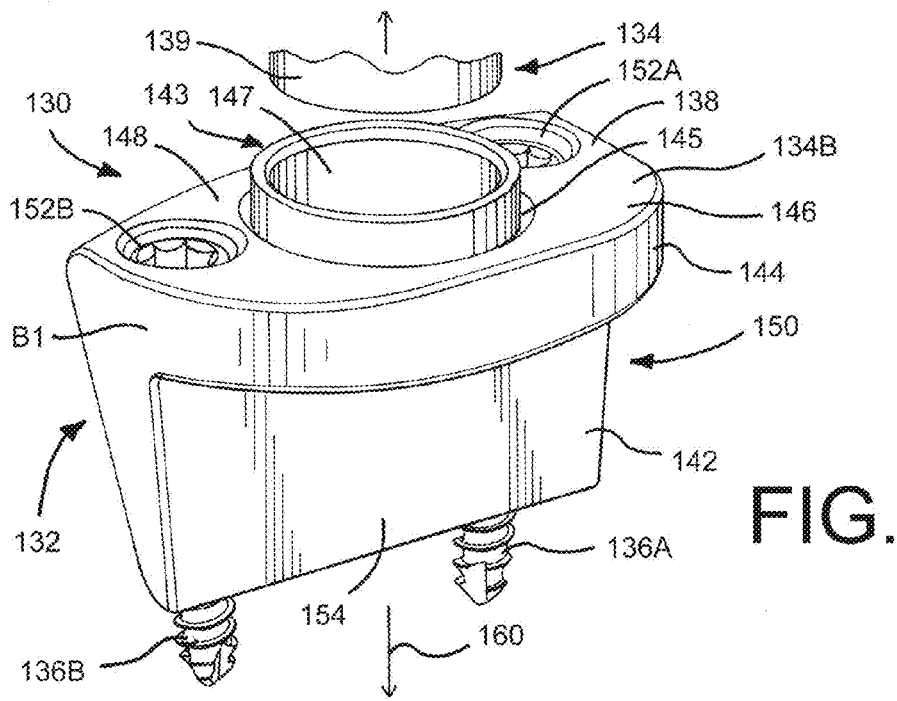
FIG. 8 is a perspective view of an alternative embodiment of the shoulder prosthesis of the present disclosure, with only a fragment of the bearing component shown.
Figure 9:
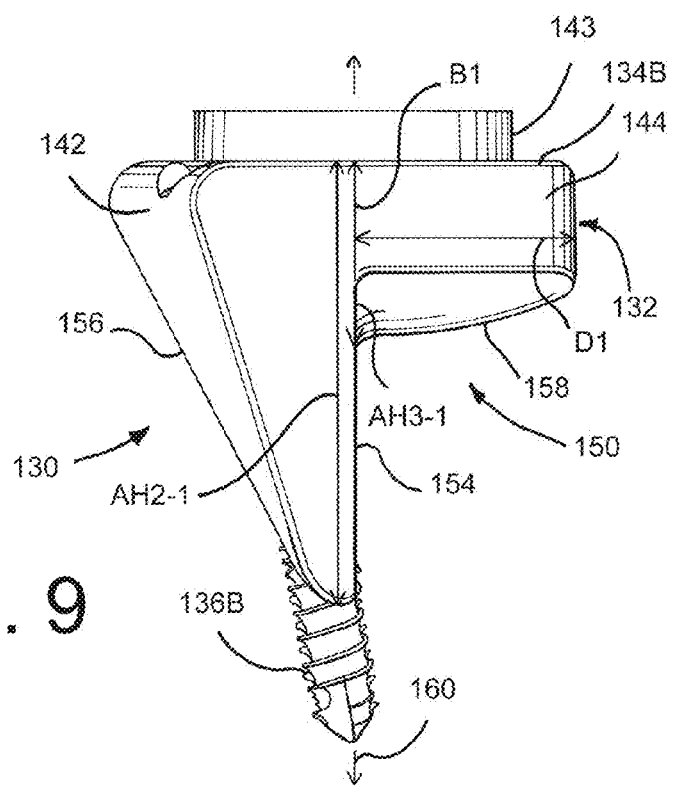
FIG. 9 is a side elevational view of the vault-filling component and the bone screws of FIG. 8.
Figure 10:
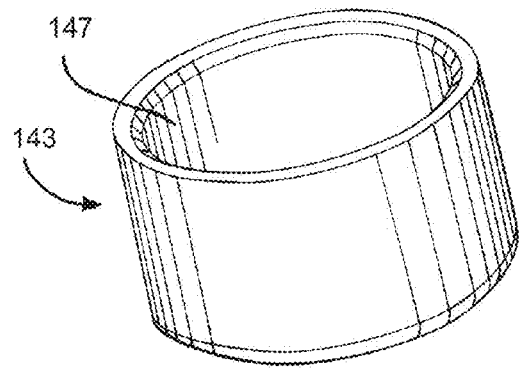
FIGS. 10 and 11 are perspective views of the insert of the vault-filling component of FIG. 8.
Figure 11:
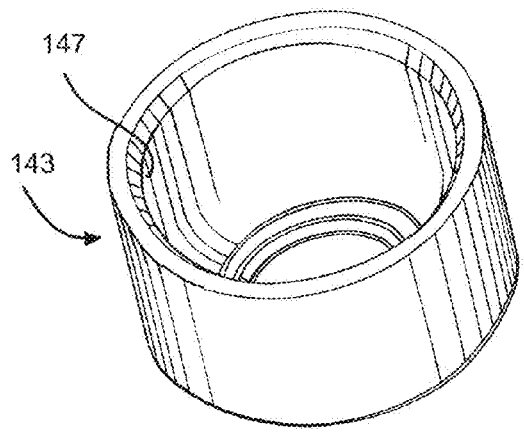

The vault-filling component 132 includes a vault-filing first portion 142 and a projecting second portion 144 which projects from the vault-filling first portion for a maximum distance D1 as shown in FIGS. 8-9. The maximum distance D1 is preferably the same as the maximum distance D of the embodiment of FIGS. 2-7. The vault-filling first portion 142 and the projecting second portion 144 are integrally formed together to form the vault-filling component. The vault-filling first portion 142 defines a first part 146 of the bearing-facing surface 138, while the projecting second portion 144 defines a second part 148 of the bearing-facing surface 138. A bone space 150 is defined between the vault-filling first portion 142 and the projecting second portion 144. In this embodiment, none of the bone attachment members 136A, 136B are positioned within the bone space 150. However, when the shoulder prosthesis 130 is implanted within a patient's scapula, subchondral and cancellous bone will be positioned within the bone space 150.

The vault-filling component 132 further defines an internally threaded fastener passage 152A and an internally threaded fastener passage 152B each extending through the component 132. The externally threaded bone screw 136A is meshingly received in the internally threaded fastener passage 152A. Similarly, the externally threaded bone screw 136B is meshingly received in the internally threaded fastener passage 152B. Rotation of each screw 136A, 136B with the fastener tool (not shown) causes advancement of each screw 136A, 136B in relation to the vault-filling component 132.

The vault-filling first portion 142 further defines a lateral surface 154 and an opposite lateral surface 156. The term "lateral" as used herein with surfaces 154, 156 means "of or relating to the sides of the vault-filling first portion 142" as opposed to any type of relation to a patient's body. The internally threaded fastener passage 152A extends between the lateral surface 154 and the lateral surface 156. The projecting second portion 144 further defines a scapula-facing surface 158. The lateral surface 154 extends downwardly from the scapula-facing surface 158 as shown in FIGS. 8-9.

The shoulder prosthesis 130 defines a central axis 160 which is generally aligned with a center of a bearing surface (not shown) of the bearing component 134. In the embodiment of FIGS. 8-11, the bearing surface of the bearing component 134 is symmetrical about the axis 160. When implanted, the axis 160 will be generally aligned with the center of the patient's natural glenoid fossa (e.g. the glenoid fossa 16 shown in FIG. 1).

A bearing body (not shown) of the bearing component 134 possesses a maximum axial height AH1-1 that represents the maximum height of the bearing body measured in a direction parallel to the axis 160. Note that the maximum axial height AH1-1 is the same as maximum axial height AH1 of the embodiment shown in FIGS. 2-7. In addition, the vault-filling first portion 142 possesses a maximum axial height AH2-1 (see FIG. 9), while the projecting second portion 144 possesses a maximum axial height AH3-1 (see FIG. 9), where both AH2-1 and AH3-1 represent maximum heights of the components (i.e. first and projecting second portions 142, 144) measured in the direction parallel to the axis 160. Note that in the embodiment of FIGS. 8-11, the maximum axial height of the projecting second portion 144 occurs at a location juxtaposed to a boundary line B1 between the vault-filling first portion 142 and the projecting second portion 144 as shown in FIG. 9. Preferably, the maximum axial height AH2-1 is the same as maximum axial height AH2 of the embodiment shown in FIGS. 2-7, and the maximum axial height AH3-1 is the same as maximum axial height AH3 of the embodiment shown in FIGS. 2-7

Figure 12:
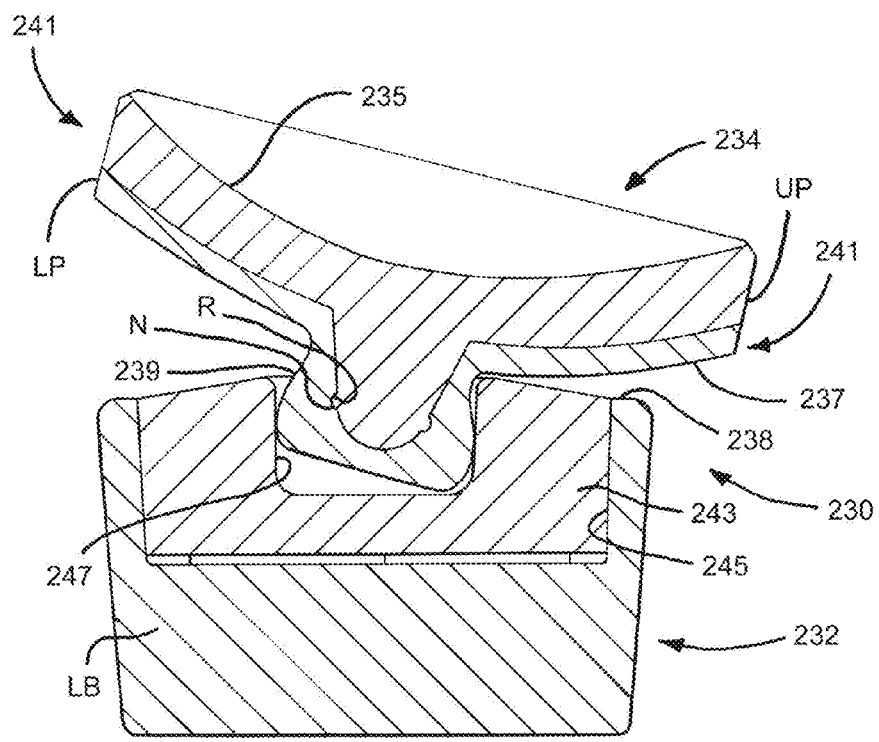
FIG. 12 is a cross-sectional view of another alternative embodiment of the shoulder prosthesis of the present disclosure.

Turning now to FIG. 12, there is shown another embodiment of a shoulder prosthesis 230 that is used in substantially the same manner as the shoulder prostheses 30 and 130 described hereinabove. The shoulder prosthesis 230 includes a vault-filling component 232 and a bearing component 234. In this embodiment, the shoulder prosthesis 230 does not include any bone attachment members such as bone attachment members 36A, 36B, 36C of the embodiment of FIGS. 2-7. Rather, bone cement may be used to attach the shoulder prosthesis 230 to a patient's scapula. Alternatively, the shoulder prosthesis 230 may be friction fit into a recess prepared in a patent's scapula, and the outer surface of the vault-filling component of the shoulder prosthesis 230 is provided with a porous-coating (except for its bearing-facing surface 238 described below) to facilitate biological ingrowth of a patient's bone. Still alternatively, the embodiment of FIG. 12 may be modified to include bone attachment members (such as those described above in connection with the embodiment of FIGS. 2-7 or the embodiment of FIGS. 8-11), as well as associated structure defining passageways within its vault-filling component to receive the bone attachment members.

The bearing component 234 includes a bearing body 241 that defines a bearing surface 235. The bearing surface 235 is a concave bearing surface configured to mate with a head of a natural humerus such as humerus 10 shown in FIG. 1 or a similarly configured prosthetic humerus. However, if the shoulder prosthesis 230 is used with a humeral prosthesis that includes a head having a concave bearing surface, then the bearing surface 235 would alternatively be configured as a convex bearing surface. The bearing body 241 of the bearing component 234 further defines a scapula-facing surface 237 which is located opposite in relation to bearing surface 235. The bearing component 234 further includes a coupling component 239 extending from the scapula-facing surface 237. In this embodiment, the coupling component 139 is a partially spherically-shaped structure as shown in FIG. 12. Also note that the bearing component 234 is made up of two parts, namely, an upper portion UP and a lower portion LP that are connected together by a notch and recess arrangement. In particular, the upper portion UP includes a downward projection that includes a pair of nubs N that are respectively received within a pair of recesses R defined in the lower portion LP. The upper portion UP is made entirely of a polymeric material, while the lower portion LP is made entirely of a metallic material. Preferably, the upper portion UP is made of the same material from which the bearing component 134 is made which was also described above, and the lower portion LP is made of the same material from which the vault-filling component 32 is made which was described above.

The vault-filling component 232 possesses the exact same dimensions and configuration as the vault-filling component 132 of the embodiment shown in FIGS. 8-11, with the following exceptions. Firstly, the vault-filling component 232 does not include any internally threaded passages defined therein such as internally threaded passages 152A, 152B of the embodiment of FIGS. 8-11. Secondly, the vault-filling component 232 includes an insert 243 that possesses a different configuration in comparison to the insert 143 of the embodiment of FIGS. 8-11. The insert 243 is configured to be received in a friction fit manner in a partially, cylindrically-shaped recess 245 defined a lower body LB of the vault-filling component 232.

The lower body LB of the vault-filling component 232 is made entirely of a metallic material. Preferably, the lower body LB of the vault-filling component 232 is made of the same material from which the vault-filling component 32 is made which was described above. The insert 243 is made of a metallic material such as a biological grade stainless steel or titanium material. The insert 243 includes an outer surface that engages the inner surface defined by the recess 245 so as to couple the insert 243 to the lower body LB of the vault-filling component 232. The insert 243 further defines a recess 247 that is configured and dimensioned to receive the coupling component 239 of the bearing component 234 in a friction fit manner so as to couple the bearing component 234 to the vault-filling component 232. It should be appreciated from FIG. 12 that the structure of the insert 243 that defines the recess 247 and the structure of the coupling component 239 allows the bearing component 234 to be coupled to the vault-filling component 232 so that the bearing surface 235 can be fixed at any of a plurality of orientations with respect to the vault-filling component 232.

Turning now to FIGS. 13-15, there is shown another embodiment of a shoulder prosthesis 330 that is used in substantially the same manner as the shoulder prosthesis 30 described hereinabove. The shoulder prosthesis 330 includes a vault-filling component 332 and a bearing component 334.

The bearing component 334 possesses the exact same dimensions and configuration as the bearing component 34. The bearing component 334 includes a bearing body 341 that defines a bearing surface 335. The bearing surface 335 is a concave bearing surface configured to mate with a head of a natural humerus such as humerus 10 shown in FIG. 1 or a similarly configured prosthetic humerus. The bearing body 341 of the bearing component 334 further defines a scapula-facing surface 337 which is located opposite in relation to bearing surface 335 as shown in FIGS. 13-14. The bearing component 334 further includes a coupling component 339 extending from the scapula-facing surface 337. In this embodiment of FIGS. 13-15, the coupling component 339 is a tapered post.

The vault-filling component 332 is made entirely of a metallic material, while the bearing component 334 is made entirely of a polymeric material. Preferably, the vault-filling component 332 is made of the same material from which the vault-filling component 32 is made which was described above. In addition, the bearing component 334 is made of the same material from which the bearing component 34 is made which was also described above.

The vault-filling component 332 defines a bearing-facing surface 338. The vault-filling component 332 includes a coupling component 340 defined by a tapered recess 340 as shown in FIGS. 13-14. The tapered recess 340 and the tapered post 339 are configured to cooperate with each other to couple the bearing component 334 to the vault-filling component 332. In particular, the tapered post 339 is received within the tapered recess 340 in a friction fit manner.

The vault-filling component 332 includes a vault-filling first portion 342 and a projecting second portion 344 which projects from the vault-filling first portion for a maximum distance D3 as shown in FIG. 13. The maximum distance D3 is preferably the same as the maximum distance D of the embodiment of FIGS. 2-7. The vault-filling first portion 342 and the projecting second portion 344 are integrally formed together to form the vault-filling component. A boundary line B3 occurs between the vault-filling first portion 342 and the projecting second portion 344 as shown in FIG. 13. The vault-filling first portion 342 defines a first part 346 of the bearing-facing surface 338, while the projecting second portion 344 defines a second part 348 of the bearing-facing surface 338. The projecting second portion 344 also defines a scapula-facing surface 358. A bone space 350 is defined between the vault-filling first portion 342 and the projecting second portion 344.

The shoulder prosthesis 330 further includes a single bone attachment member 336. The bone attachment member 336 is a bone peg that extends from the scapula-facing surface 358 of the projecting second portion 344. The bone peg 336 includes a plurality of outwardly extending fins as shown in FIG. 13. When the shoulder prosthesis is implanted in a patient's scapula, both the scapula-facing surface 358 and the lateral surface 354 will be positioned in contact with subchondral and/or cancellous bone located within a glenoid vault of the scapula. Also, the bone peg 336, including its outwardly extending fins, will be positioned in contact with subchondral and/or cancellous bone located within a glenoid vault of the scapula.

The vault-filling first portion 342 further defines a lateral surface 354 and an opposite lateral surface 356. The lateral surface 354 extends downwardly from the scapula-facing surface 358 as shown in FIG. 13, while the lateral surface 356 extends downwardly from the first part 346 of the bearing-facing surface 338. The surfaces 354, 356 converge as the vault-filling first portion 342 extends in a downward direction. The two surfaces 354, 356 then meet at the distal end of the first portion 342.

The shoulder prosthesis 330 defines a central axis 360 which is generally aligned with a center of a bearing surface 335 of the bearing component 334. In the embodiment of FIGS. 13-15, the bearing surface 335 of the bearing component 334 is symmetrical about the axis 360. When the shoulder prosthesis 330 is implanted, the axis 360 will generally be aligned with the center of the patient's natural glenoid fossa (e.g. the glenoid fossa 16 shown in FIG. 1).

The bearing body 341 of the bearing component 334 possesses a maximum axial height AH1-3 that represents the maximum height of the bearing body measured in a direction parallel to the axis 360. Note that the maximum axial height AH1-3 is the same as the maximum axial height AH1 of the embodiment shown in FIGS. 2-7. In addition, the vault-filling first portion 342 possesses a maximum axial height AH2-3 (see FIG. 13), while the projecting second portion 344 possesses a maximum axial height AH3-3 (see FIG. 13), where both AH2-3 and AH3-3 represent maximum heights of the components (i.e. first and projecting second portions 342, 344) measured in the direction parallel to the axis 360. Preferably, the maximum axial height AH2-3 is the same as maximum axial height AH2 of the embodiment shown in FIGS. 2-7, and the maximum axial height AH3-3 is the same as maximum axial height AH3 of the embodiment shown in FIGS. 2-7.

FIG. 13A shows an alternative vault-filling component 332A that may be substituted for the vault-filling component 332 for use in the shoulder prosthesis 330. As shown in FIG. 13A, the vault-filling component 332A is configured exactly the same as the vault-filling component 332, with one exception. In particular, a vault-filling first portion 342A of the vault-filling component 332A is modular whereby a distal portion DP of the vault-filling first portion 342A may be removably coupled to a proximal portion PP of the vault-filling first portion 342A. To this end, the distal portion DP includes a tapered post TP that is configured to be received in a tapered recess TR of the proximal portion PP in a friction fit manner.

Figure 16:
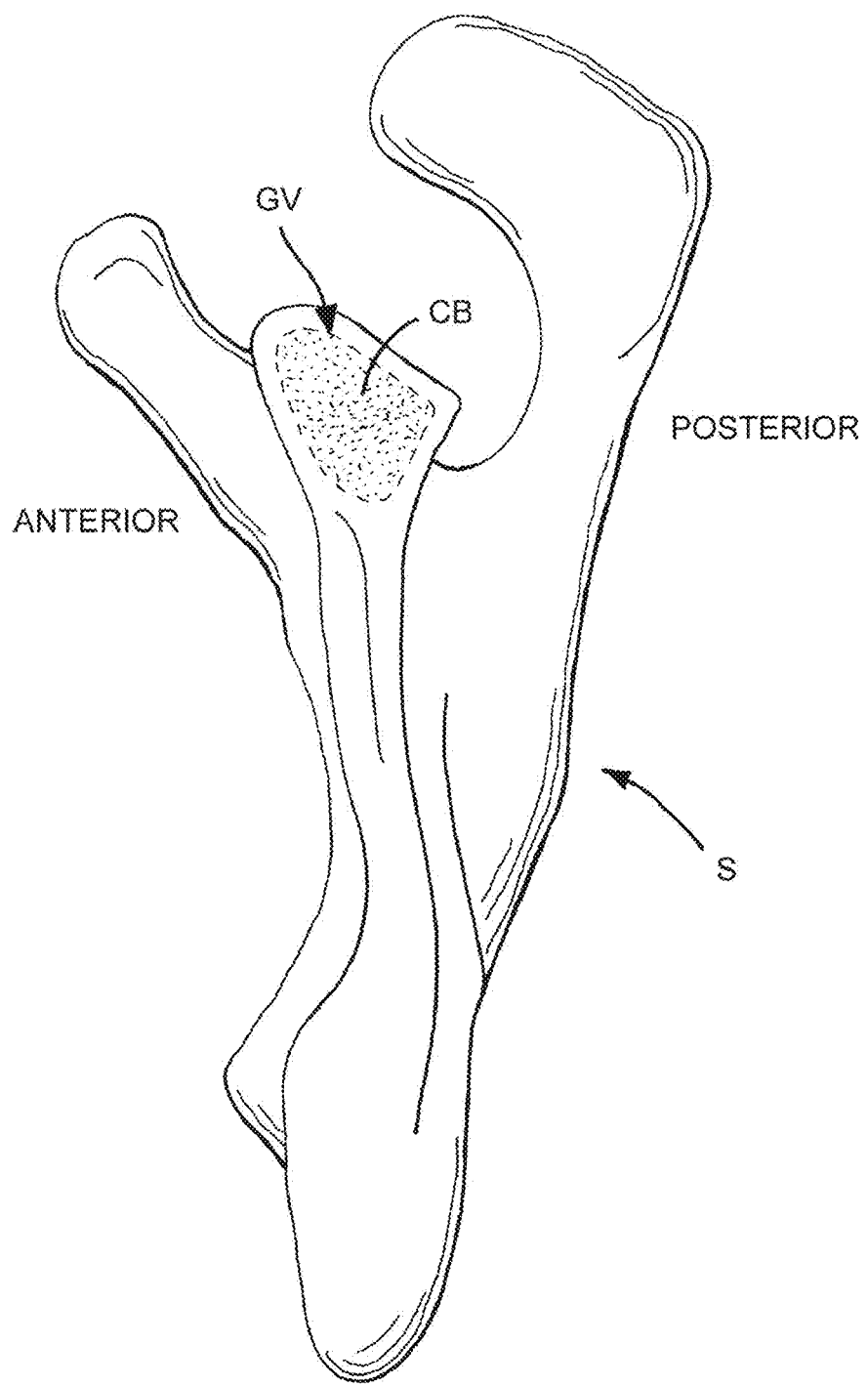
FIG. 16 is an inferior view of a patient's scapula in which the shoulder prosthesis of FIG. 13 may be implanted.

In accordance with the present disclosure, a method of securing the shoulder prosthesis 330 to a scapula S is disclosed with reference to FIGS. 16-19. FIG. 16 shows an inferior view of the scapula S. The scapula S has an anterior side and a posterior side as identified in FIG. 17. The scapula further has a glenoid vault GV and cancellous bone CB located within the glenoid vault GV.

Figure 17:
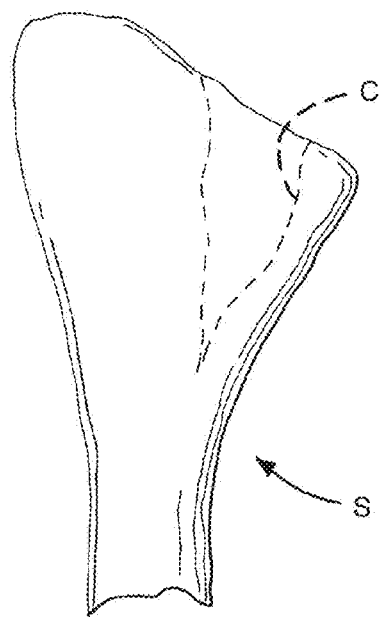
FIG. 17 is a fragmentary view of the patient's scapula of FIG. 16 showing its deterioration whereby a cavity has been formed therein.
Figure 18:
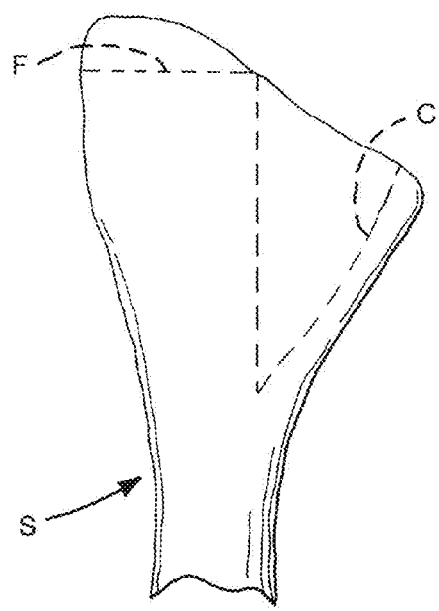
FIG. 18 is a fragmentary view of the patient's scapula of FIG. 17 after certain portions of it have been resurfaced for receipt of the shoulder prosthesis of FIG. 13.
Figure 19:
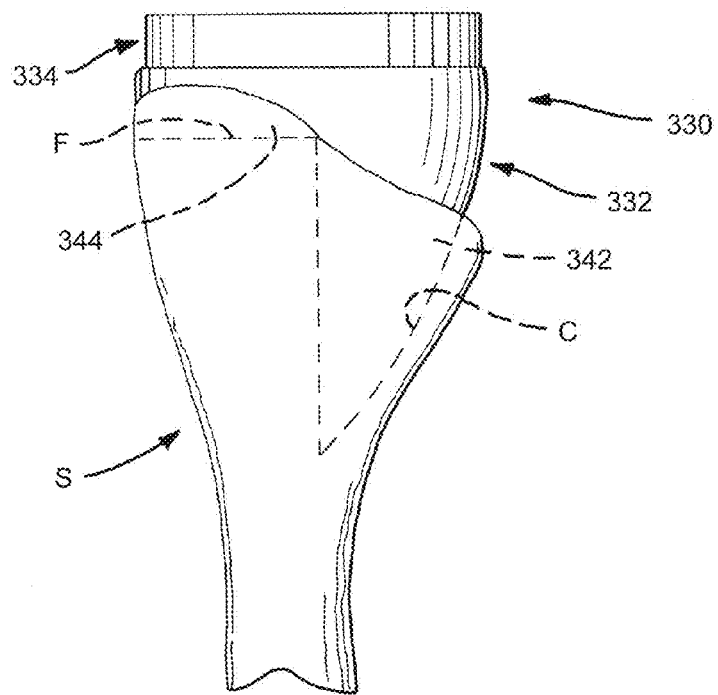
FIG. 19 is a fragmentary view of the patient's scapula of FIG. 18 after implantation of the shoulder prosthesis of FIG. 13 therein.

In FIG. 17, there is shown a fragmentary view of the scapula S depicting its glenoid region. As can be seen in FIG. 17, certain aspects of the subchondral bone support surface and underlying cancellous bone located within the glenoid vault have significantly deteriorated whereby a cavity C has formed. In preparation for implantation of the shoulder prosthesis 330, bone of the scapula S is removed by surgically preparing surfaces of the glenoid vault GV with bone shaping tools such as reamers, saws, drills, burrs, rasps, and the like. In particular, a flat surface F of subchondral and/or cancellous bone is created as shown in FIG. 18. Further, the cavity C is slightly enlarged and the walls thereof evened out so as to be configured to receive the complementary shaped vault-filling component 332 of the shoulder prosthesis 330. Also, a bore (not shown) is created in the subchondral and/or cancellous bone CB by drilling on the flat surface F in a direction perpendicular thereto, the bore being configured to receive the bone anchor 336 in a friction fit manner. Thereafter, the vault-filling component 332 of the shoulder prosthesis 330 is positioned so that (i) the vault-filling first portion 342 is located within the glenoid vault GV, (ii) the bone anchor 336 is positioned within the bore defined in the subchondral and/or cancellous bone CB, and (iii) the scapula-facing surface 358 of the projecting second portion 344 is positioned in contact with the flat surface F defined by the subchondral and/or cancellous bone CB so that subchondral and/or cancellous bone CB is located within the bone space 350. Thereafter, the bearing component 334 is coupled to the vault-filling component 332 by advancing the tapered post 339 into the tapered recess 340 in a friction fit manner.

There is a plurality of advantages arising from the various features of each of the embodiments of the shoulder prosthesis described herein. It will be noted that alternative embodiments of the shoulder prosthesis may not include all of the features described yet still benefit from at least some of the advantages of such features. Those of ordinary skill in the art may readily devise their own implementations of the shoulder prosthesis that incorporates one or more of the features and fall within the spirit and scope of the present invention as defined by the appended claims.

While bone screws, bone anchors, bone cement, and porous coating have been described as being effective individually to secure the shoulder prostheses 30, 130, 230, 330 to a patient's scapula, it should be appreciated that any combination of these mechanisms may be used with any of the prosthesis described herein to secure the prosthesis to the scapula. Alternatively, other mechanisms may be used individually or in combination with the above described securing mechanisms to fix the shoulder prostheses 30, 130, 230, 330 to a patient's scapula. For example, biocompatible plastic or metallic wires or bands may be used to fix the shoulder prostheses 30, 130, 230, 330 to a patient's scapula.

What is claimed is:

1. A shoulder prosthesis, comprising:
a vault-filling component defining a bearing-facing surface and having a first coupling component, said vault-filling component including (i) a vault-filling first portion defining a first part of said bearing-facing surface, and (ii) a projecting second portion projecting from said vault-filling first portion so as to define a second part of said bearing-facing surface, said vault-filling first portion and said projecting second portion defining a bone space therebetween,
a bearing component defining a bearing surface and having a second coupling component configured to cooperate with said first coupling component to couple said bearing component to said vault-filling component;
a first externally threaded bone screw extending into said bone space; and
a second externally threaded bone screw extending into in said bone space,
wherein said projecting second portion of said vault-filling component further defines a scapula-facing surface,
wherein said vault-filling first portion of said vault-filling component further defines (i) a first lateral surface extending from said scapula-facing surface, and (ii) a second lateral surface located opposite to said first lateral surface, and
wherein said first lateral surface and at least a portion of said second lateral surface taper towards each other in a direction extending away from said bearing-facing surface,
wherein (i) said vault-filling first portion includes a first internally threaded fastener passage extending therethrough, and (ii) said first externally threaded bone screw is meshingly received in said first internally threaded fastener passage,
wherein (i) said projecting second portion includes a second internally threaded fastener passage extending therethrough, and (ii) said second externally threaded bone screw is meshingly received in said second internally threaded fastener passage,
wherein said first internally threaded fastener passage extends from said first lateral surface to said second lateral surface, and
wherein said second internally threaded fastener passage extends from said second part of said bearing-facing surface to said scapula-facing surface.

2. The shoulder prosthesis of claim 1, wherein:
said vault-filling component is comprised of a metallic material, and
said bearing component is comprised of a polymeric material.

3. The shoulder prosthesis of claim 1, wherein:
said bearing component possesses a first maximum axial height of at least 3.0 mm,
said vault-filling first portion possesses a second maximum axial height of at least 15.0 mm, and
said projecting second portion possesses a third maximum axial height of at least 1.0 mm.

4. The shoulder prosthesis of claim 3, wherein said projecting second portion extends from said vault-filling first portion for a maximum distance of at least 2.0 mm.

5. The shoulder prosthesis of claim 1, wherein:
said first coupling component includes one of a tapered post and a tapered recess, and
said second coupling component includes the other of a tapered post and a tapered recess.

6. The shoulder prosthesis of claim 5, wherein:
said bearing component defines a back surface opposite said bearing-facing surface,
said second coupling component includes said tapered post,
said tapered post extends from said back surface,
said first coupling component includes said tapered recess, and
said tapered post is configured to be received in said tapered recess in a friction fit manner.

7. The shoulder prosthesis of claim 1, wherein said bearing surface of said bearing component is one of a concave bearing surface and a convex bearing surface.

8. The shoulder prosthesis of claim 1, wherein said vault-filling first portion and said projecting second portion are integrally formed together to form said vault-filling component.

9. The shoulder prosthesis of claim 1, wherein said second lateral surface of said vault-filling first portion extends from said first part of said bearing-facing surface to said first lateral surface of said vault-filling first portion.

10. The shoulder prosthesis of claim 1, wherein said second lateral surface extends from said first part of said bearing-facing surface.

11. The shoulder prosthesis of claim 1, wherein said first lateral surface and said portion of said second lateral surface converge together to form a distal end portion of said vault-filling component.

12. A shoulder prosthesis, comprising:
a metallic vault-filling component defining a bearing-facing surface and having a first coupling component, said metallic vault-filling component including (i) a metallic vault-filling first portion defining a first part of said bearing-facing surface, and (ii) a metallic projecting second portion projecting from said metallic vault-filling first portion so as to define a second part of said bearing-facing surface, said metallic vault-filling first portion and said metallic projecting second portion defining a bone space therebetween;

a first externally threaded bone screw extending into said bone space;

a second externally threaded bone screw extending into in said bone space; and a polymeric bearing component defining a bearing surface and having a second coupling component configured to cooperate with said first coupling component to couple said polymeric bearing component to said metallic vault-filling component, wherein said metallic projecting second portion of said metallic vault-filling component further defines a scapula-facing surface, wherein said metallic vault-filling first portion of said metallic vault-filling component further defines (i) a first lateral surface extending from said scapula-facing surface, and (ii) a second lateral surface extending from said first part of said bearing-facing surface, wherein said first lateral surface and said second lateral surface taper towards each other in a direction extending away from said bearing-facing surface, wherein (i) said metallic vault-filling first portion includes a first internally threaded fastener passage extending therethrough, and (ii) said first externally threaded bone screw is meshingly received in said first internally threaded fastener passage, wherein (i) said metallic projecting second portion includes a second internally threaded fastener passage extending therethrough, and (ii) said second externally threaded bone screw is meshingly received in said second internally threaded fastener passage, wherein said first internally threaded fastener passage extends from said first lateral surface to said second lateral surface, and wherein said second internally threaded fastener passage extends from said second part of said bearing-facing surface to said scapula-facing surface.

13. The shoulder prosthesis of claim 12, wherein:
said polymeric bearing component has a first maximum axial height of at least 3.0 mm,
said metallic vault-filling first portion has a second maximum axial height of at least 15.0 mm,
said metallic projecting second portion has a third maximum axial height of at least 1.0 mm, and
said metallic projecting second portion extends from said metallic vault-filling first portion for a maximum distance of at least 2.0 mm.

14. The shoulder prosthesis of claim 12, wherein:
said polymeric bearing component defines a back surface opposite said bearing-facing surface,
said second coupling component includes a tapered post,
said tapered post extends from said back surface,
said first coupling component includes a tapered recess,
said tapered recess is defined in said metallic vault-filling component, and
said tapered post is configured to be received in said tapered recess in a friction fit manner.

15. The shoulder prosthesis of claim 12, wherein said second lateral surface of said metallic vault-filling first portion extends from said first part of said bearing-facing surface to said first lateral surface of said metallic vault-filling first portion.

* * * * *